(12) United States Patent
Krzysik et al.

(10) Patent No.: US 6,515,029 B1
(45) Date of Patent: *Feb. 4, 2003

(54) ABSORBENT ARTICLE HAVING A HYDROPHILIC LOTIONIZED BODYSIDE LINER

(75) Inventors: Duane Gerard Krzysik, Appleton, WI (US); David Charles Musil, Neenah, WI (US); Frank Andrew Rosch, III, Sherwood, WI (US); Gordon Allen Shaw, Greenville, WI (US); Diane Michele Underhill, Neenah, WI (US); Jeffrey Michael Hockersmith, Mill Creek, WA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/298,313

(22) Filed: Apr. 23, 1999

(51) Int. Cl.$^7$ .................. A61K 31/045; A61K 7/48; A61K 31/00; A61K 47/00; A61L 15/16
(52) U.S. Cl. .................. 514/738; 424/402; 424/443; 424/445; 424/446; 424/447; 514/60; 514/463; 514/715; 514/722; 514/723; 514/724; 514/772; 514/778; 514/969; 604/358; 604/363; 604/364; 604/378; 604/385.01
(58) Field of Search .................. 424/443, 402, 424/404, 445, 446, 447; 604/358, 317, 363, 385.1, 385.2, 364, 378, 385.01; 514/60, 463, 715, 722, 723, 724, 738, 772, 778, 969

(56) References Cited

U.S. PATENT DOCUMENTS

| | | | |
|---|---|---|---|
| 3,305,392 A | 2/1967 | Britt ..................... 428/211 |
| 3,585,998 A | 6/1971 | Hayford et al. ............ 604/359 |
| 3,724,465 A | 4/1973 | Duchane .................. 604/363 |
| 3,756,238 A | 9/1973 | Hanke ..................... 604/287 |
| 3,814,101 A | 6/1974 | Kozak ..................... 604/370 |
| 3,821,350 A | 6/1974 | Suchane ................... 264/257 |
| 3,881,488 A | 5/1975 | Delanty et al. ............ 604/374 |
| 3,896,807 A | 7/1975 | Buchalter ................. 604/289 |
| 3,902,493 A | 9/1975 | Baier et al. .............. 604/286 |
| 4,040,857 A | 8/1977 | Lissant ................... 106/243 |
| 4,100,324 A | 7/1978 | Anderson et al. ........... 442/344 |
| 4,164,563 A | 8/1979 | Chang ..................... 514/10 |
| 4,273,786 A | 6/1981 | Kraskin ................... 514/566 |
| 4,343,783 A | 8/1982 | Hooper et al. ............. 424/401 |
| 4,355,020 A | 10/1982 | Kuy ........................ 424/404 |
| 4,355,046 A | 10/1982 | Suess ..................... 514/712 |
| 4,556,560 A | 12/1985 | Buckingham ............... 424/641 |
| 4,604,313 A | 8/1986 | McFarland et al. ......... 428/172 |
| 4,613,447 A | 9/1986 | Hara et al. ............... 15/104.93 |
| 4,623,339 A | 11/1986 | Ciraldo et al. ............ 604/359 |
| 4,634,438 A | 1/1987 | Sustmann et al. .......... 604/376 |
| 4,634,439 A | 1/1987 | Sustmann et al. .......... 604/376 |
| 4,637,820 A | 1/1987 | Marini et al. ............. 8/129 |
| 4,655,756 A | 4/1987 | Fawkes ................... 604/360 |
| 4,657,537 A | 4/1987 | Zimmerer ................. 604/360 |
| 4,675,014 A | 6/1987 | Sustmann et al. .......... 604/375 |
| 4,685,909 A | 8/1987 | Berg et al. ............... 604/360 |
| 4,711,780 A | 12/1987 | Fahim .................... 424/641 |
| 4,732,797 A | 3/1988 | Johnson et al. ............ 428/74 |
| 4,738,678 A | 4/1988 | Paulis ................... 604/385.201 |
| 4,753,643 A | 6/1988 | Kassai ................... 604/359 |
| 4,753,647 A | 6/1988 | Curtis ................... 604/385.06 |
| 4,760,096 A | 7/1988 | Sakai et al. ............. 514/786 |
| 4,772,501 A | 9/1988 | Johnson et al. ........... 428/74 |
| 4,790,836 A | 12/1988 | Brecher .................. 604/359 |
| 4,790,840 A | 12/1988 | Cortina .................. 604/385.06 |
| 4,798,603 A | 1/1989 | Meyer et al. ............. 604/378 |
| 4,808,175 A | 2/1989 | Hansen ................... 604/385.06 |
| 4,834,737 A | 5/1989 | Khan ..................... 604/385.14 |
| 4,861,405 A | 8/1989 | Kassai ................... 156/204 |
| 488,204 A | 11/1989 | Tenenbaum ................ 427/180 |
| 4,911,932 A | 3/1990 | Clum et al. .............. 424/642 |

(List continued on next page.)

FOREIGN PATENT DOCUMENTS

| | | |
|---|---|---|
| CA | 2019557 A1 | 12/1990 |
| DE | 35 36 318 A1 | 4/1987 |
| DE | 4136540 A1 | 11/1990 |
| EP | 0 212 870 B1 | 7/1986 |
| EP | 0 613 675 A1 | 9/1994 |
| EP | 0 797 968 A1 | 10/1997 |
| EP | 0 808 151 B1 | 11/1997 |
| EP | 0 815 841 A1 | 1/1998 |

(List continued on next page.)

OTHER PUBLICATIONS

American Society for Testing Materials (ASTM) Designation: D1321–92, "Standard Test Method for Needle Penetration of Petroleum Waxes", Nov. 15, 1992, 3 pages.

(List continued on next page.)

Primary Examiner—Michael G. Hartley
Assistant Examiner—Frank Choi
(74) Attorney, Agent, or Firm—Jeffrey B Curtin; Alysse A Dudkowski

(57) ABSTRACT

An absorbent article having a bodyside liner includes a hydrophilic lotion formulation on the outer bodyfacing surface thereof. The hydrophilic lotion formulation comprises from about 10 to about 90 weight percent of a hydrophilic solvent, from about 5 to about 90 weight percent of a high molecular weight polyethylene glycol, and from about 0 to about 60 weight percent of a fatty alcohol. The hydrophilic lotion formulation has a reduced adverse effect on the absorbent and liquid uptake properties of the liner and the absorbent body when compared to conventional lipophilic or hydrophobic lotion formulations. The hydrophilic lotion formulation acts as a lubricant to reduce the abrasion of the skin caused by the liner and also transfers to the skin to provide improved skin health.

33 Claims, 4 Drawing Sheets

U.S. PATENT DOCUMENTS

| | | | |
|---|---|---|---|
| 4,931,052 A | 6/1990 | Feldman | 604/385.06 |
| 4,960,592 A | 10/1990 | Hagen et al. | 424/537 |
| 4,978,534 A | 12/1990 | Saitoh | 424/484 |
| 4,990,144 A | 2/1991 | Blott | 604/304 |
| 4,996,238 A | 2/1991 | Matravers | 514/63 |
| 5,043,155 A | 8/1991 | Puchalski et al. | 714/772.5 |
| 5,049,440 A | 9/1991 | Bornhoeft, III et al. | 442/123 |
| 5,110,593 A | 5/1992 | Benford | 424/401 |
| 5,139,790 A | 8/1992 | Snipes | 424/435 |
| 5,141,803 A | 8/1992 | Pregozen | 442/123 |
| 5,147,576 A | 9/1992 | Montague et al. | 510/417 |
| 5,176,668 A | 1/1993 | Bernardin | 604/368 |
| 5,176,672 A | 1/1993 | Bruemmer et al. | 604/385.19 |
| 5,192,277 A | 3/1993 | Chung et al. | 604/360 |
| 5,192,606 A | 3/1993 | Proxmire et al. | 428/171 |
| 5,194,261 A | 3/1993 | Pichierre | 424/401 |
| 5,232,691 A | 8/1993 | Lemole | 424/78.02 |
| 5,244,668 A | 9/1993 | Snipes | 424/435 |
| 5,306,486 A | 4/1994 | McCook et al. | 424/59 |
| 5,336,212 A | 8/1994 | De Francesco | 604/360 |
| 5,336,486 A | 8/1994 | Gans et al.. | 514/772 |
| 5,350,624 A | 9/1994 | Georger et al. | 428/219 |
| 5,362,488 A | 11/1994 | Sibley et al. | 424/78.05 |
| 5,364,382 A | 11/1994 | Latimer et al. | 604/378 |
| 5,376,655 A | 12/1994 | Imaki et al. | 514/237.5 |
| 5,384,125 A | 1/1995 | Dipippo et al. | 514/23 |
| 5,436,007 A | 7/1995 | Hartung et al. | 424/402 |
| 5,466,232 A | 11/1995 | Cadieux et al. | 604/378 |
| 5,482,765 A | 1/1996 | Bradley et al. | 442/382 |
| 5,486,166 A | 1/1996 | Bishop et al. | 604/366 |
| 5,490,846 A | 2/1996 | Ellis et al. | 604/366 |
| 5,496,298 A | 3/1996 | Kuepper et al. | 604/389 |
| 5,509,915 A | 4/1996 | Hanson et al. | 604/378 |
| 5,525,346 A | 6/1996 | Hartung et al. | 424/402 |
| 5,533,990 A | 7/1996 | Yeo | 604/363 |
| 5,569,230 A | 10/1996 | Fisher et al. | 604/385.06 |
| 5,578,310 A | 11/1996 | M'Timkulu et al. | 424/401 |
| 5,601,871 A | 2/1997 | Krzysik et al. | 427/288 |
| 5,605,749 A | 2/1997 | Pike et al. | 442/60 |
| 5,607,760 A | 3/1997 | Roe | 442/375 |
| 5,607,980 A | 3/1997 | McAfee et al. | 514/476 |
| 5,609,587 A | 3/1997 | Roe | 604/360 |
| 5,614,293 A | 3/1997 | Krzysik et al. | 428/211 |
| 5,618,529 A | 4/1997 | Pickierri | 424/78.06 |
| 5,618,850 A | 4/1997 | Coury et al. | 514/772.2 |
| 5,631,012 A | 5/1997 | Shanni | 424/401 |
| 5,635,191 A | 6/1997 | Roe et al. | 424/402 |
| 5,643,588 A | 7/1997 | Roe et al. | 424/402 |
| 5,643,899 A | 7/1997 | Elias et al. | 514/171 |
| 5,648,083 A | 7/1997 | Blieszner et al. | 424/402 |
| 5,650,218 A | 7/1997 | Krzysik et al. | 428/195 |
| 5,652,049 A | 7/1997 | Suzuki | 442/387 |
| 5,652,194 A | 7/1997 | Dyer et al. | 502/402 |
| 5,658,559 A | 8/1997 | Smith | 424/78.02 |
| 5,665,368 A | 9/1997 | McCormack | 442/389 |
| 5,693,037 A | 12/1997 | Lee et al. | 604/381 |
| 5,738,859 A | 4/1998 | Posner | 424/401 |
| 5,801,107 A | 9/1998 | Everhart et al. | 442/408 |
| 5,830,487 A | 11/1998 | Klofta et al. | 424/402 |
| 5,843,056 A | 12/1998 | Good et al. | 604/367 |
| 5,849,314 A | 12/1998 | Dobkowski et al. | 424/401 |
| 5,855,897 A | 1/1999 | Pelle | 424/401 |
| 5,855,999 A | 1/1999 | McCormack | 604/370 |
| 5,856,245 A | 1/1999 | Caldwell et al. | 442/76 |
| 5,869,033 A | 2/1999 | Schulz | 424/78.02 |
| 5,869,075 A | 2/1999 | Krzysik | 424/414 |
| 5,869,172 A | 2/1999 | Caldwell | 428/306.6 |
| 5,871,763 A | 2/1999 | Luu et al. | 424/402 |
| 5,879,341 A | 3/1999 | Odorzynski et al. | 604/367 |
| 5,891,126 A | 4/1999 | Osborn, III et al. | 604/385.17 |
| 5,938,649 A | 8/1999 | Ducker et al. | 604/363 |
| 5,944,705 A | 8/1999 | Ducker et al. | 604/364 |
| 5,951,990 A | 9/1999 | Ptchelintsev | 424/401 |
| 5,989,577 A | 11/1999 | Hoath et al. | 424/402 |
| 5,990,377 A | 11/1999 | Chen et al. | 604/381 |
| 6,004,566 A | 12/1999 | Friedman et al. | 424/400 |
| 6,051,749 A | 4/2000 | Schulz | 604/368 |
| 6,075,179 A | 6/2000 | McCormack et al. | 604/367 |
| 6,100,442 A | 8/2000 | Samuelsson et al. | 604/385.01 |
| 6,103,245 A | 8/2000 | Clark et al. | 424/401 |
| 6,107,537 A * | 8/2000 | Elder et al. | 604/364 |
| 6,117,439 A | 9/2000 | Kake | 424/404 |
| 6,118,041 A | 9/2000 | Roe et al. | 604/360 |
| 6,120,488 A | 9/2000 | VanRijswijck et al. | 604/385.28 |
| 6,136,332 A | 10/2000 | Grollier et al. | 424/404 |
| 6,149,934 A * | 11/2000 | Krzysik et al. | 424/443 |
| 6,152,906 A | 11/2000 | Faulks et al. | 604/385.01 |
| 6,153,209 A | 11/2000 | Vega et al. | 424/404 |
| 6,156,024 A | 12/2000 | Schulte et al. | 604/385.28 |
| 6,166,285 A | 12/2000 | Schulte et al. | 604/364 |
| 6,183,766 B1 | 2/2001 | Sine et al. | 424/409 |
| 6,217,890 B1 | 4/2001 | Paul et al. | 424/402 |
| 6,238,682 B1 | 5/2001 | Klofta et al. | 424/402 |
| 6,287,581 B1 | 9/2001 | Krzysik et al. | 424/402 |
| 6,294,186 B1 | 9/2001 | Beerse et al. | 424/405 |
| 6,309,736 B1 | 10/2001 | McCormack et al. | 428/198 |
| 6,316,030 B1 | 11/2001 | Kropf et al. | 424/489 |
| 6,344,218 B1 | 2/2002 | Dodd et al. | 424/605 |
| 6,355,022 B1 | 3/2002 | Osborn III et al. | 604/385.17 |
| 2001/0006666 A1 | 7/2001 | Harbeck | 424/401 |

FOREIGN PATENT DOCUMENTS

| | | |
|---|---|---|
| EP | 0 875 233 A1 | 11/1998 |
| EP | 0 922 452 A1 | 6/1999 |
| EP | 0 922 456 A1 | 6/1999 |
| EP | 1 057 476 A1 | 12/2000 |
| GB | 880276 | 10/1961 |
| GB | 884688 | 12/1961 |
| GB | 2033751 A | 5/1980 |
| GB | 2 311 727 A | 10/1997 |
| WO | WO 90/12555 A1 | 11/1990 |
| WO | WO 92/09289 A1 | 6/1992 |
| WO | WO 93/16670 A1 | 9/1993 |
| WO | WO 93/21878 A1 | 11/1993 |
| WO | WO 94/09757 A1 | 5/1994 |
| WO | WO 94/09796 A1 | 5/1994 |
| WO | WO 95/19190 A1 | 7/1995 |
| WO | WO 96/16681 A1 | 6/1996 |
| WO | WO 96/16682 A1 | 6/1996 |
| WO | WO 97/05908 A2 | 2/1997 |
| WO | WO 97/05909 A2 | 2/1997 |
| WO | WO 97/38735 A1 | 10/1997 |
| WO | WO 97/38738 1 | 10/1997 |
| WO | WO 98/00858 A1 | 1/1998 |
| WO | WO 98/03147 A1 | 1/1998 |
| WO | WO 98/47546 A1 | 10/1998 |
| WO | WO 99/12530 A1 | 3/1999 |
| WO | WO 99/13861 A1 | 3/1999 |
| WO | WO 99/26610 A1 | 6/1999 |
| WO | WO 99/26618 | 6/1999 |
| WO | WO 99/26619 A1 | 6/1999 |
| WO | WO 99/45771 A1 | 9/1999 |
| WO | WO 99/45973 A1 | 9/1999 |
| WO | WO 99/45974 A1 | 9/1999 |
| WO | WO 99/45976 A1 | 9/1999 |
| WO | WO 99/ 46316 A2 | 9/1999 |
| WO | WO 00/38747 A2 | 7/2000 |
| WO | WO 00/64501 A1 | 11/2000 |
| WO | WO 00/64503 A1 | 11/2000 |
| WO | WO 00/69481 A1 | 11/2000 |
| WO | WO 00/69482 A1 | 11/2000 |

| | | |
|---|---|---|
| WO | WO 00/69483 A1 | 11/2000 |
| WO | WO 00/69484 A1 | 11/2000 |
| WO | WO 00/71177 A1 | 11/2000 |

OTHER PUBLICATIONS

American Society for Testing Materials (ASTM) Designation: D3236–88, "Standard Test Method for Apparent Viscosity of Hot Melt Adhesives and Coating Materials", Oct. 31, 1988, 6 pages.

Akin, Frank J.; Lemmen, Jac T.; Bozarth, Dena L.; Garofalo, Martin J.; and Grove, Gary L.; "A refined method to evaluate diapers for effectiveness in reducing skin hydration using the adult forearm," *Skin Research and Technology*, ISSN 0909–752X, 1997, pp. 173–176.

Berg, Ronald W., Ph.D; Milligan, Michael C., M.B.A.; and Sarbaugh, Frank C.; "Association of Skin Wetness and pH with Diaper Dermatitis," *Pediatric Dermatology*, Mar., 1994, vol. 11, Nov. 1, pp. 18–20.

Imai, Satoshi and Kuwabara, Chihiro; Pigeon Co., Ltd., Ibaragi, Japan; "Infant Skin and Its Care," *Cosmetics & Toiletries*, vol. 107, Jul., 1992, pp. 85–86, 88–90.

Preston, Sandra L., PharmD & Bryant, Bobby G., MS, PharmD; "Etiology and Treatment of Diaper Dermatitis," *Hospital Pharmacy*, 1994, vol. 29, No. 12, pp. 1086–1088, 1097.

Sires, Ulrike I., MD & Mallory, Susan B., MD; "Diaper dermatitis," *Postgraduate Medicine*, vol. 98, No. 6, Dec., 1995, pp. 79–82, 84, 86.

Zielinski, Ruth, C.N.M., Hanson, Elizabeth, C.N.M.; "Diaper Dermatitis: Medical Aspects of Skin Care," *Nonwovens World*, Feb.–Mar., 2000, pp. 60–65.

Patent Abstracts of Japan 02043265 A: Description of Masaru et al., "THIXOTROPIC SEMISOLID COMPOSITION." (1990).

Patent Abstracts of Japan 02053709 A: Description of Masaru et al., "THIXOTROPIC SEMISOLID COMPOSITION." (1990).

Patent Abstracts of Japan 06065104 A: description of Michio, "POWDER COMPOSITION FOR DERMATIC APPLICATION PREVENTED FROM SCATTERABLILITY." (1994).

Patent Abstracts of Japan 07267839 A: Description of Yoshiko et al., "OINTMENT COMPOSITION ADHESIVE TO ORAL MUCOSA." (1999).

Patent Abstracts of Japan 09151112 A: Description of Yasuhiro et al., "MICROEMULSION COMPOSITON." (1997).

Patent Abstracts of Japan 10037070 A: Description of Takeo., "ANTIMICROBIAL FIBER CONTAINING CATECHIN OF GREEN TEA COMPONENT." (1998).

Patent Abstracts of Japan 10306039 A: Description of Christine et al., "SOLID TOPICAL AQUEOUS COMPOSITION CAPABLE OF FORMING FILM, WHEN APPLIED, AND HAVING GEL APPEARANCE." (1998).

Patent Abstracts of Japan 55025430 A: Description of Mikio et al., "THICKENING AND GELLING AGENT." (1980).

Patent Abstracts of Japan 56110611 A: Description of Mitsue et al., "PREPARATION OF OINTMENT EMBROCATION FOR SKIN." (1981).

Patent Abstracts of Japan 59053409 A: Description of Susumu et al., "BASE COMPOSITION AND PHARMACEUTICAL COMPOSITION FOR EXTERNAL USE." (1984).

Patent Abstracts of Japan 59122420 A: Description of Katsuo et al., "LOCAL OINTMENT" (1984).

Patent Abstracts of Japan 59227816 A: Description of Kenji et al., "SKIN CLEANING AND WIPING AGENT COMPOSITION" (1984).

Patent Abstracts of Japan 60006759 A: Description of Tadashi et al., "WATER–DISPERSIBLE RESIN FOR CATAPLASM." (1985).

Patent Abstracts of Japan 61129117 A: Description of Sakahito et al., "ALOE–CONTAINING CATAPLASM." (1986).

Patent Abstracts of Japan 61194014 A: Description of Hiroshi et al., "HYDROPHILIC BASE." (1986).

Patent Abstracts of Japan 63264413 A: Description of Kazuo, "GABEXATE MESYLATE OINTMENT." (1988).

Federal Test Method Standard (FTMS) No. 191A, Method 5450, "Permeability To Air; Cloth; Calibrated Orifice Method," Jul. 20, 1978, 5 pages.

Federal Test Method Standard (FTMS) No. 191A, Method 5514, "Water Resistance of Cloth; Low Range, Hydrostatic Pressure Method," Jul. 20, 1978 3 pages.

Barbero, G.J. et al., "Stool Trypsin and Chymotrypsin," *American Journal of Diseases of Children*, vol. 112, Jul. through Dec. 1966, pp. 536–540.

Barry, B.W. and A.J. Grace, "Investigation of Semisolid Lipophilic Preparations by Small Strain and Continuous Shear Viscometry and Their Application to Texture Profile," *Journal of Pharmaceutical Sciences*, vol. 60, No. 6, Jun. 1971, pp. 814–820.

Boylan, James C., "Rheological Study of Selected Pharmaceutical Semisolids," *Journal of Pharmaceutical Sciences*, vol. 55, No. 7, Jul. 1966, pp. 710–715.

Bremecker, K.D. et al., "Novel concept for a Mucosal Adhesive Ointment," *Journal of Pharmaceutical Sciences*, vol. 73, No. 4, Apr. 1984, pp. 548–552.

Davies, Oven L. and Peter L. Goldsmith, editors, *Statistical Methods in Research and Production*, Fourth Revised Edition, published by Longman Inc., New York, 1984, p. 460.

Davis, S.S. et al., "Some Limitations of Continuous Shear Methods for the Study of Pharmaceutical Semi–Solids," *Journal of Pharmacy and Pharmacology*, vol. 20, Supplemental Issue, Dec. 1968, pp. 157S–167S.

Drechsler, Lee Ellen et al., "The Wipe: A Carrier of Skin Benefits," *Cosmetics & Toiletries*, vol. 116, No. 10, Oct. 2001, pp. 33–36, 38, 40, 42.

Eccleston, G.M. et al., "Correlation of Viscoelastic Functions for Pharmaceutical Semisolids: Comparison of Creep and Oscillatory Tests for Oil–in–Water Creams Stabilized by Mixed Emulsifiers," *Journal of Pharmaceutical Sciences*, vol. 62, No. 12, Dec. 1973, 1954–1961.

Eccleston, G.M., "Structure and Rheology of Cetomacrogol Creams: The Influence of Alcohol Chain Length and Homologue Composition," *Journal of Pharmacy and Pharmacology*, vol. 29, No. 3, Mar. 1977, pp. 157–162.

Eros, I. and A. Thaleb, "Rheological Studies of Creams: I. Rheological Functions and Structure of Creams," *Acta Pharmaceutica Hungarica*, vol. 64, No. 3, May 1994, pp. 101–103.

Fuhrer, C., "Gel Structure of Fatty Alcohols in Ointment Bases," *Pharmazie*, vol. 26, No. 1, Jan. 1971, pp. 43–5. (German).

Haverback, Bernard J. et al., "Measurement of Trypsin and Chymotrypsin in Stool: A Diagnostic Test for Pancreatic Exocrine Insuffieciency," *Gastroenterology*, vol 44, 1963, pp. 588–597.

Huttenrauch, R., "Activation Energies in Plastic Deformation of Ointment Gels," *Pharmazie*, vol. 28, No. 4, Apr. 1973, 244–249. (German).

Kedzierewicz, F. et al., "Preparation of Silicoane Microshperes by Emulsion Polymerization: Application to the Encapsulation of a Hydrophilic Drug," *Journal of Microencapsulation*, vol 15, No. 2, Mar.–Apr. 1998, pp. 227–236.

Muguet, V. et al., "Formulation of Shear Rate Sensitive Multiple Emulsions," *Journal of Controlled Release*, vol. 70, No. 1–2, Jan. 29, 2001, pp. 37–49.

Odio, Mauricio R. et al., "Continuous Topical Administration of a Petrolatum Formulation by a Novel Disposable Diaper. 1. Effect on Skin Surface Microtopography," *Dermatology*, 2000;200(3):232–237.

Odio, Mauricio R. et al., "Continuous Topical Administration of a Petrolatum Formulation by a Novel Disposable Diaper. 2. Effect on Skin Condition," *Dermatology*, 2000;200(3):238–243.

Pena, Lorraine E. et al., "Structural Rheology of a Model Ointment," *Pharmaceutical Research*, vol. 11, No. 6, Jun. 1994, pp. 875–881.

Popovici, Luliana et al., "The Physico–Chemical Characterization and Therapeutic Evaluation of Cicatrol," Rivista Medico–Chirurgicala Societatii Medici si Naturalisti din Lasi, vol. 96, No. 1–2, Jan. –Jun. 1992, pp. 57–64.

Salo, D.P. et al., "Ion Exchange Properties of Clay Minerals and Its Use for Obtaining Clays With Planned Properties. 3. Effect of the Nature of Exchange Kation on the Structure–Mechanical Properties of Suspensions and Ointment Bases Prepared From Clays of Montmorillonite and Sepiolite–Mountain Leather Groups," *Farm Zh*, vol. 23, No. 6, 1968, pp. 61–66. (Ukrainian).

Taleb, A. and I. Eros, "Rheolgical Studies of Creams. II. Effect of Water Content on Rheological Characteristics," *Acta Pharmaceutica Hungarica*, vol. 66, No. 2, Mar. 1996. pp. 71–76.

Tamburic, S. et al., "An Investigation Into the Use of Thermorheology and Texture Analysis in the evaluation of W/O Creams Stabilized With a Silicone Emulsifier," *Pharmaceutical Development Technology*, vol. 1, no. 3, Oct. 1996, pp. 299–306.

Vinson, Joe and John Proch, "Inhibition of Moisture Penetration to the Skin by a Novel Incontinence Barrier Product," *Journal of Wound Ostomy Continence Nursing*, vol. 25, No. 5, Sep. 1998, pp. 256–260.

\* cited by examiner

ABSORBENT ARTICLE HAVING A HYDROPHILIC LOTIONIZED BODYSIDE LINER

BACKGROUND OF THE INVENTION

1. Field of the Invention

The present invention relates to absorbent articles for absorbing body fluids and exudates, such as urine and fecal material. More particularly, the present invention relates to absorbent garments, such as disposable diapers and adult incontinence garments, which include a hydrophilic lotionized bodyside liner for improved skin health benefits.

2. Description of the Related Art

Conventional absorbent articles, such as disposable diapers, employ absorbent materials located between a liquid pervious bodyside liner and a liquid impermeable outer cover to absorb body exudates. Such conventional absorbent articles have typically included elasticized waistbands and leg cuffs to help reduce the leakage of body exudates. Some conventional absorbent articles have also included elasticized containment or barrier flaps at the leg or waist sections of the article to further reduce leaks.

Typically, the liquid pervious bodyside liners have been constructed of nonwoven materials such as spunbond polyolefin materials. Unfortunately, such materials do not always provide a soft, nonabrasive contact with the skin. In particular, during continuous use of absorbent articles containing such liners, the wearer's skin can become quite irritated and red particularly in the presence of urine and feces. The abrasion resulting from such liners and the presence of urine and feces can undesirably lead to the onset of diaper dermatitis (diaper rash). Diaper dermatitis can afflict almost every infant at some time during the diaper wearing years. Although other factors influence the onset of diaper dermatitis, critical factors include the abrasiveness of the bodyside liner and the hydration level of the wearer's skin.

To prevent body exudates from contacting the wearer's skin, the caregiver often applies skin protective products directly to the skin of the wearer before positioning the article on the wearer. Such products have included petrolatum, mineral oil, talc, corn starch, or various other commercially available rash creams or hydrophilic lotions. This procedure typically involves the caregiver applying the products to their hand and then transferring the products to the wearer's skin.

To eliminate the caregiver from contacting the products and to reduce skin abrasion and improve skin health, hydrophilic lotion formulations can be applied to the bodyside liners such that, in use, the hydrophilic lotion formulation either transfers to the skin or provides lubricity thereby reducing the friction between the liner and the skin. However, conventional lotion formulations have typically been hydrophobic liquids, hydrophobic semi solids, or hydrophobic solids based formulations at room temperature. However, since these lotion formulations are hydrophobic, they have sometimes adversely affected the ability of the absorbent article to accept body exudates and, in particular, urine discharges, from the wearer. As a result, the add-on amount and total surface area covered by such hydrophobic hydrophilic lotions has been limited. Moreover, the hydrophobic nature of these formulations has made it difficult to incorporate hydrophilic, cosmetic and active ingredients into the formulation Further, such formulations have been unstable and tended to migrate away from the surface of the liner into the liner and absorbent core of the absorbent articles leaving less on the surface to transfer to the skin or provide the reduced abrasion. This migration problem is particularly evident at higher temperatures such as those at the skin surface in use or those in typical storage conditions in warm climates.

Thus, conventional absorbent articles, such as those described above, have not been completely satisfactory. For example, hydrophobic lotions which have been incorporated on the liners of such articles have adversely affected the absorbency of the articles and have migrated such that a less effective amount has been applied to the wearer's skin or been located between the skin and the liner in use. As a result, the wearer's skin has remained susceptible to rashes, abrasion and irritation. Accordingly, there remains a need for absorbent articles which provide improved skin health. In particular, there remains a need for absorbent articles which include a hydrophilic lotion on the bodyside liner which does not adversely affect absorbency, which exhibits reduced migration, and in which other ingredients are readily incorporated.

SUMMARY OF THE INVENTION

In response to the difficulties and problems discussed above, a new disposable absorbent article which has an improved hydrophilic lotionized bodyside liner has been discovered. In particular, it has been discovered that a superior hydrophilic lotion treated bodyside liner for an absorbent article can be made by (1) applying to the outer bodyfacing surface of the bodyside liner, a melted moisturizing/protective/healing hydrophilic lotion formulation comprising a hydrophilic solvent, a polyethylene glycol having as molecular weight of at least about 720 and a fatty alcohol; and (2) resolidifying the formulation to form a distribution, preferably a uniform distribution, of solid deposits on the bodyfacing surface of the liner. Because the formulation is a solid at room temperature and rapidly solidifies after deposition, it has less tendency to penetrate and migrate into the liner and absorbent body of the article during processing and at elevated storage temperatures. Compared to liners treated with liquid or semi-solid hydrophobic formulations, the hydrophilic lotion formulations of the present invention have a reduced adverse affect on absorbency and leave a greater percentage of the added formulation on the bodyfacing surface of the liner where it can contact and transfer to the wearer's skin to provide a benefit.

When employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

As used herein, the term "viscosity" refers to the viscosity in centipoises determined according to ASTM D3236, entitled "Standard Test Method for Apparent Viscosity of Hot Melt Adhesives and Coating Materials."

As used herein, the phrase "melting point" refers to the temperature at which the majority of the melting occurs, it being recognized that melting actually occurs over a range of temperatures.

As used herein, the phrase "melt point viscosity" refers to the viscosity of the formulation at the temperature at which the majority of the melting occurs, it being recognized that melting actually occurs over a range of temperatures.

As used herein, the phrase "penetration hardness" refers to the needle penetration in millimeters according to ASTM D 1321, "Needle Penetration of Petroleum High molecular weight polyethylene glycoles." Lower needle penetration hardness values correspond to harder materials.

As used herein, the term "z-direction migration loss" refers to the value obtained when subjecting an absorbent article having a hydrophilic lotion formulation on the bodyfacing surface thereof to the Z-Direction Lotion Migration Test set forth below.

As used herein, the term "cd-direction migration loss" refers to the value obtained when subjecting an absorbent article having a lotion formulation on the bodyfacing surface thereof to the CD-Direction Lotion Migration Test set forth below.

In one aspect, the present invention resides in an absorbent article having a bodyside liner which includes a hydrophilic lotion formulation on the outer bodyfacing surface thereof. The hydrophilic lotion formulation comprises from about 10 to about 90 weight percent of a hydrophilic solvent, from about 5 to about 90 weight percent of a high molecular weight polyethylene glycol, and from about 0 to about 60 weight percent of a fatty alcohol.

In a particular embodiment, the hydrophilic lotion formulation is applied to the bodyside liner at a temperature no more than about 10° C. above a melting point of the hydrophilic lotion formulation to reduce migration of the hydrophilic lotion formulation on the bodyside liner.

In another aspect, the invention resides in an absorbent article which includes an outer cover, a liquid permeable bodyside liner which defines a bodyfacing surface and which is connected in superposed relation to the outer cover, and an absorbent body which is located between the bodyside liner and said outer cover. The absorbent article also includes a hydrophilic lotion formulation on at least a portion of the bodyfacing surface of the bodyside liner. The hydrophilic lotion formulation includes a hydrophilic solvent and the article defines a z-direction migration loss of no more than about 55% when subjected to the Z-Directional Lotion Migration Test set forth herein.

In some embodiments, the hydrophilic solvent is selected from the group consisting of propylene glycol, polyethylene glycols with an average molecular weight of less than 720, glycerin, sorbitol solutions, methoxyisopropanol, PPG-2 propyl ether, PPG-2 butyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, hydrogenated starch hydrolysates, silicone glycols, and the like and mixtures thereof.

Moreover, in some embodiments, the polyethylene glycol is selected from the group consisting of PEG 6000 polyethylene glycol, PEG 8000 polyethylene glycol, PEG 10000 polyethylene glycol and mixtures thereof. Further, in some embodiments, the fatty alcohol is selected from the group consisting of $C_{14}$ to $C_{30}$ or greater fatty alcohols.

For example, in a particular aspect, the present invention provides an absorbent article which includes an outer cover; a liquid permeable bodyside liner which defines a bodyfacing surface and which is connected in superposed relation to the outer cover, and an absorbent body which is located between the bodyside liner and the outer cover. The absorbent article also includes a hydrophilic lotion formulation on at least a portion of the bodyfacing surface of the bodyside liner which includes from about 30 to about 70 weight percent of a solvent selected from the group consisting of propylene glycol, low molecular weight polyethylene glycol and mixtures thereof, from about 15 to about 25 weight percent polyethylene glycol selected from the group consisting of PEG 6000 polyethylene glycol, PEG 8000 polyethylene glycol, PEG 10000 polyethylene glycol and mixtures thereof, and from about 15 to about 25 weight percent of a fatty alcohol selected from the group consisting of stearyl alcohol, behenyl alcohol and mixtures thereof based on a total weight of the hydrophilic lotion formulation.

The various aspects of the present invention advantageously provide an absorbent article with improved skin health benefits. In particular, the hydrophilic lotionized liner provides a soft, smooth contact with the wearer's skin and reduced levels of skin irritation. Moreover, because the hydrophilic lotion formulations applied to the liner are more stable and have a higher viscosity than conventional hydrophilic lotion formulations, particularly at higher temperatures, a greater percentage of the added hydrophilic lotion remains on the surface of the liner where it can readily contact and transfer to the wearer's skin to provide the benefit. Further, if desired, a lower amount of the hydrophilic lotion formulation can be added to the liner to provide the same benefit at a lower cost due to the localization of the hydrophilic lotion at the surface of the liner.

Moreover, since the hydrophilic lotion formulations applied to the liner of the absorbent articles of the present invention are hydrophilic, the absorbent articles have maintained high levels of absorbency and rapid liquid intake. As such, the hydrophilic lotions can be applied in greater amounts and over greater percentages of the overall surface area on the bodyside liner for improved transfer to the skin and resulting skin health. As a result, the skin of the wearers of such absorbent articles should remain less susceptible to rashes, abrasion and irritation.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
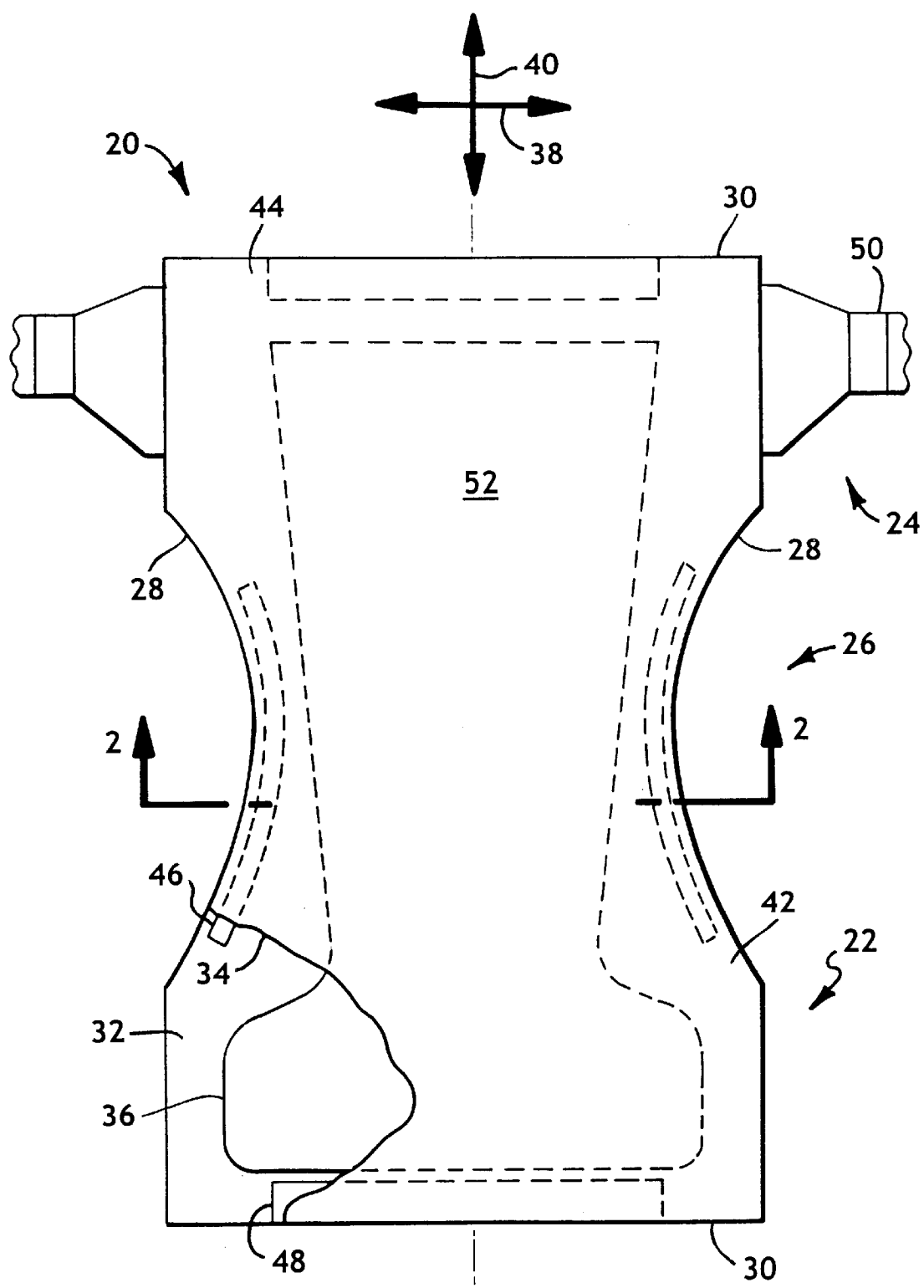
FIG. 1 representatively shows a partially cut away, top plan view of an absorbent article according to one embodiment of the invention in a stretched and laid flat condition with the surface of the article which contacts the skin of the wearer facing the viewer.
Figure 2:
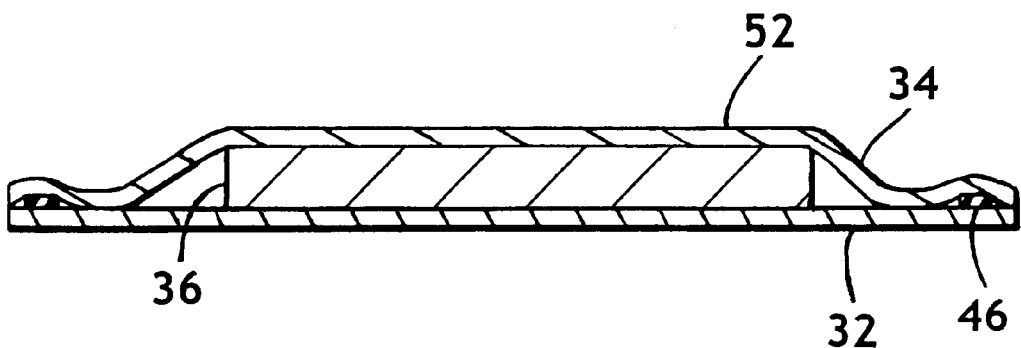
FIG. 2 representatively shows a sectional view of the absorbent article of FIG. 1 taken along line 2—2.

With reference to FIGS. 1 and 2, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable outer cover 32, a porous, liquid permeable bodyside liner 34 positioned in facing relation with the outer cover 32, and an absorbent body 36, such as an absorbent pad, which is located between the outer cover and the bodyside liner. The diaper 20 also defines a lateral direction 38 and a longitudinal direction 40. Marginal portions of the diaper 20, such as marginal sections of the outer cover 32, may extend past the terminal edges of the absorbent body 36. In the illustrated embodiment, for example, the outer cover 32 extends outwardly beyond the terminal marginal edges of the absorbent body 36 to form side margins 42 and end margins 44 of the diaper 20. The bodyside liner 34 is generally coextensive with the outer cover 32 but may optionally cover an area which is larger or smaller than the area of the outer cover 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIGS. 1 and 2, the elastic members 46 and 48 are illustrated in their uncontracted, stretched condition for the purpose of clarity. The diaper 20 may also include a pair of elasticized, longitudinally extending containment flaps (not shown) which are configured to maintain an upright, perpendicular arrangement in at least the intermediate section 26 of the diaper 20 to serve as an additional barrier to the lateral flow of body exudates. Suitable constructions and arrangements of containment flaps are well known to those skilled in the art.

Alternatively, the diaper 20 may include a pair of separate, elasticized and gathered leg gussets (not shown) or combination leg gussets/containment flaps (not shown) which are attached to the diaper along the side margins 42 in at least the intermediate section 26 of the diaper 20 to provide elasticized leg cuffs. Such gussets or combination gussets/flaps may be configured to extend beyond and bridge across the respective concave portion of the side margins 42.

The diaper 20, as representatively illustrated in FIGS. 1 and 2, may further include a pair of fasteners 50 employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction 38 of the diaper 20.

The diaper 20 may further include a surge management layer (not shown) positioned between the bodyside liner 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of surge management layers are well known to those skilled in the art. Other suitable diaper components may also be incorporated on absorbent articles of the present invention.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the bodyside liner 34 and outer cover 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 article by employing the above-identified attachment mechanisms.

The outer cover 32 of the diaper 20, as representatively illustrated in FIGS. 1 and 2, may suitably be composed of a material which is either liquid permeable or liquid impermeable. It is generally preferred that the outer cover 32 be formed from a material which is substantially impermeable to liquids. For example, a typical outer cover can be manufactured from a thin plastic film or other flexible liquid impermeable material. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art. Further, the outer cover 32 may be formed of a woven or nonwoven fibrous web layer which has been totally or partially constructed or treated to impart a desired level of liquid impermeability to selected regions that are adjacent or proximate the absorbent body 36.

Desirably, the outer cover 32 may be composed of a "breathable" material which permits vapors to escape from the absorbent body 36 while still preventing liquid exudates from passing through the outer cover 32. For example, the outer cover 20 is desirably constructed to be permeable to at least water vapor and has a water vapor transmission rate of at least about 1000 g/sq.m/24 hr., desirably at least about 1500 g/sq.m24 hr, more desirably at least about 2000 g/sq.m/24 hr., and even more desirably at least about 3000 g/sq.m/24. Materials which have a water vapor transmission rate less than those above do not allow a sufficient amount of air exchange and undesirably result in increased levels of skin hydration. As used herein, the phrase "water vapor transmission rate" (WVTR) refers to the WVTR value according to the Water Vapor Transmission Rate Test which is described in further detail herein below.

In a particular embodiment, the outer cover 20 is provided by a microporous film/nonwoven laminate material comprising a spunbond nonwoven material laminated to a microporous film. For example, the laminate may include a 0.6 osy (20.4 gsm) polypropylene spunbond material thermally attached to a 18.7 gsm stretched microporous film. The film may include from about 20 percent to about 75 percent by weight calcium carbonate particulates and the remainder primarily linear low density polyethylene. The film is then stretched which causes the polyethylene component to stretch while the particulates remain unstretched, thus causing voids to develop around the calcium carbonate particles in the film. The resulting laminate may define a water vapor transmission rate of from about 1000 to about 5000 g/sq.m/24 hr.

Examples of suitable breathable materials for the outer cover 20 are also described in U.S. Pat. No. 5,879,341 issued Mar. 9, 1999 in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE OUTER COVER"; and U.S. Pat. No. 5,855,999 issued Jan. 5, 1999 to McCormack et al. and entitled "BREATHABLE, CLOTH-LIKE FILM/NONWOVEN COMPOSITE", the disclosures of which are herein incorporated by reference.

The absorbent body 36 of the diaper 20, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Virginia and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The bodyside liner 34, as representatively illustrated in FIGS. 1 and 2, suitably presents a bodyfacing surface which is compliant, soft feeling, and nonirritating to the wearer's skin. Further, the bodyside liner 34 may be less hydrophilic than the absorbent body 36, to present a relatively dry surface to the wearer, and may be sufficiently porous to be liquid permeable, permitting liquid to readily penetrate through its thickness. A suitable bodyside liner 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 34 is suitably employed to help isolate the wearer's skin from liquids held in the absorbent body 36.

Various woven and nonwoven fabrics can be used for the bodyside liner 34. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity.

In a particular embodiment of the present invention, the bodyside liner 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.3 weight percent of a surfactant mixture which contains a mixture of AHCOVEL Base N-62 and GLUCOPAN 220UP surfactant in a 3:1 ratio based on a total weight of the surfactant mixture. The AHCOVEL Base N-62 is purchased from Hodgson Textile Chemicals Inc., a business having offices in Mount Holly, and includes a blend of hydrogenated ethoxylated castor oil and sorbitan monooleate in a 55:45 weight ratio. The GLUCOPAN 220UP is purchased from Henkel Corporation and includes alkyl polyglycoside. The surfactant may be applied by any conventional means, such as spraying, printing, brush coating or the like. The surfactant may be applied to the entire bodyside liner 34 or may be selectively applied to particular sections of the bodyside liner 34, such as the medial section along the longitudinal centerline of the diaper, to provide greater wettability of such sections.

The bodyside liner 34 of the absorbent article of the present invention further includes a hydrophilic lotion formulation on the outer bodyfacing surface 52 thereof. The hydrophilic lotion formulation generally includes a hydrophilic solvent or hydrophilic solvent, a high molecular weight polyethylene glycol and a fatty alcohol. For example, the hydrophilic lotion formulation may include from about 10 to about 90 weight percent of a hydrophilic solvent, from about 5 to about 90 weight percent of a polyethylene glycol having a molecular weight of at least about 720, and from about 0 to about 60 weight percent of a fatty alcohol based on a total weight of the hydrophilic lotion formulation. The hydrophilic lotion formulation may include other ingredients as well.

The hydrophilic solvent acts as a lubricant to reduce the abrasiveness of the bodyside liner to the skin and, upon transfer to the skin, helps to maintain the soft, smooth and pliable appearance of the skin. Suitable hydrophilic solvents which can be incorporated into the hydrophilic lotion formulation include, but are not limited to, water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol, hydrogenated starch hydrolysate, silicone glycols, and the like. For example, a particularly well suited hydrophilic solvent is propylene glycol. Other hydrophilic solvents may also be added in a manner which maintains the desired properties of the hydrophilic lotion formulations set forth herein. The solvent may further function as an emollient, occlusive agent, moisturizer, barrier enhancer and combinations thereof.

To provide the improved stability and transfer to the skin of the wearer, the hydrophilic lotion formulation may include from about 10 to about 90 weight percent, desirably from about 25 to about 75 weight percent, and more desirably from about 30 to about 70 weight percent of the hydrophilic solvent. Hydrophilic lotion formulations which include an amount of hydrophilic solvent greater than the recited amounts tend to have lower melt point viscosities and higher penetration values which undesirably leads to migration of the hydrophilic lotion. Whereas, hydrophilic lotion formulations which include an amount of hydrophilic solvent less than the recited amounts tend to have low penetration values to provide less transfer to the wearer's skin.

The high molecular weight polyethylene glycol in the hydrophilic lotion formulations of the present invention primarily functions as an immobilizing agent and a melt point viscosity modifier for the hydrophilic solvent and any active ingredient. In addition to immobilizing the solvent, modifying it's viscosity and reducing it's tendency to migrate, the high molecular weight polyethylene glycol in the hydrophilic lotion formulation provides a tackiness to the hydrophilic lotion formulation which improves the transfer to the skin of the wearer. As used herein, high molecular weight polyethylene glycols are polyethylene glycols having an average molecular weight of 720 or greater. These materials are not liquid at room temperature. Particularly suitable high molecular weight polyethylene glycols can have an average molecular weight of from about 720 to about 1,840,000, more specifically from about 1400 to about 440,000, and still more specifically from about 1760 to about 10,570.

To provide the improved transfer to the skin of the wearer and migration stability, the hydrophilic lotion formulation may include from about 5 to about 90 weight percent, desirably from about 10 to about 50 weight percent, and more desirably from about 15 to about 25 weight percent of the high molecular weight polyethylene glycol. Hydrophilic lotion formulations which include an amount of high molecular weight polyethylene glycol less than the recited amounts tend to have lower viscosities and higher penetration values which undesirably leads to migration of the hydrophilic lotion. Whereas, hydrophilic lotion formulations which include an amount of high molecular weight polyethylene glycol greater than the recited amounts tend to provide less transfer to the wearer's skin.

The fatty alcohol in the hydrophilic lotion formulations of the present invention functions as a co-immobilizing agent, feel enhancer, emollient, lubricant, and transfer enhancer. Suitable fatty alcohols include, but are not limited to, alcohols having a carbon chain length of $C_4$–$C_{30}$, including cetyl alcohol, stearyl alcohol, arachidyl alcohol, and behenyl alcohol and the like and mixtures thereof. The hydrophilic lotion formulation may include from about 0 to about 60 weight percent, desirably from about 10 to about 30 weight percent, and more desirably from about 15 to about 25 weight percent of the fatty alcohol for improved performance.

In a particularly preferred embodiment, the hydrophilic lotion formulation may include from about 30 to about 70 weight percent of a solvent selected from the group consisting of propylene glycol, low molecular weight polyethylene glycol and mixtures thereof, from about 15 to about 25 weight percent polyethylene glycol selected from the group consisting of PEG 6000 polyethylene glycol, PEG 8000 polyethylene glycol, PEG 10000 polyethylene glycol, and mixtures thereof, and from about 15 to about 25 weight percent of a fatty alcohol selected from the group consisting of stearyl alcohol, behenyl alcohol and mixtures thereof based on a total weight of the hydrophilic lotion formulation.

Optionally, an additional viscosity enhancer may also be added to the hydrophilic lotion formulation to increase the viscosity to help stabilize the formulation on the bodyfacing surface 52 of the bodyside liner 34 and thereby reduce migration and improve transfer to the-skin. Desirably, the viscosity enhancer increases the viscosity of the hydrophilic lotion formulation by at least about 50 percent, more desirably by at least about 500 percent and even more desirably by at least about 1000 percent. Suitable viscosity enhancers which can be incorporated into the hydrophilic lotion formulation include natural hydrophilic gums, resins, starches, and flours, modified natural gums and resins, and synthetic polymers, gums and resins, soaps or mixtures thereof. For example, suitable viscosity enhancers include, but are not limited to, acacia, acrylamides copolymer, agar, algin, carrageean, carbomer, carboxymethyl chitin, carboxymethyl chitin, carboxymethyl hydroxyetyl cellulose, carboxymethyl hydroxypropyl guar, cellulose gum, cetyl hydroxyetyl cellulose, corn starch, corn syrup, dextrin, ethylene/sodium acrylate copolymer, gelatin, gellan gum, glyceryl alginate, guar gum, Hydroxybutyl methyl cellulose, hydroxyetylcellulose, hydroxyethyl ethylcellulose, hydroxypropylcellulose, hydroxypropyl chitosan, hydroxypropyl guar, hydroxypropyl methylcellulose, karaya gum, kelp, microcrystalline cellulose, methyl cellulose, methyl hydroxyethylcellulose, natto gum, oat flour, polyacrylic acid, polyvinyl alcohol, potassium alginate, potassium aluminum polyacrylate, potassium carrageenan, potassium polyacrylate, potato starch, propylene glycol alginate, sclerotium gum, sodium acrylate/vinyl alcohol copolymer, sodium carboxymetyl chitin, sodium carboxymethyl dextran, sodium carrageenan, sodium Isooctylene/MA copolymer, sodium polyacrylate starch, sodium polymethacrylate, sodium stearate, starch/acrylates/acrylamide copolymer, tragacanth gum, tromethamine acrylates/acrylonitrogens copolymer, wheat flour, wheat starch, xanthan gum, and the like and mixtures thereof The hydrophilic lotion formulation may include from about 0 to about 25 weight percent, desirably form about 0 to about 10 weight percent, and more desirably from about 0 to about 5 weight percent of the viscosity enhancer for reduced migration, process control and/or improved transfer to the wearer's skin.

If it is desired that the hydrophilic lotion formulation treat the skin, it can also include an active ingredient such as a diaper rash skin protectant. Skin protectants include drug products which protects injured or exposed skin or mucous membrane surface from harmful or annoying stimuli. Suitable active ingredients which can be incorporated into the hydrophilic lotion formulation include alantoin and its derivatives, aluminum hydroxide gel, calamine, cocoa butter, dimethicone, cod liver oil, glycerin, kaolin and its derivatives, lanolin and its derivatives, mineral oil, shark liver oil, talc, topical starch, zinc acetate, zinc carbonate, and zinc oxide and the like, and mixtures thereof. The lotion formulation may include from about 0.10 to about 95 weight percent of the active ingredient depending upon the skin protectant and the amount desired to be transferred to the skin.

In order to better enhance the benefits to the wearer, additional ingredients can be included in the hydrophilic lotion formulations of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); humectants (increase the water content of the top layers of the skin); natural moisturizing agents (NMF) and other skin moisturizing ingredients known in the art; opacifiers (reduce the clarity or transparent appearance of the product); skin conditioning agents; other solvents (liquids employed to dissolve components found useful in the cosmetics or drugs); and surfactants (as cleansing agents, emulsifying agents, solubilizing agents, and suspending agents).

An important property of the hydrophilic lotion formulations of the different aspects of the present invention is their ability to remain on the surface of the bodyside liner and their resistance to migration into the article such that they can readily be transferred to the wearer's skin. In this regard, the articles having the hydrophilic lotion formulations of the present invention applied to there bodyside liner define a z-direction migration loss of no more than about 55%, desirably no more than about 50%, more desirably no more than about 45%, even more desirably no more than about 40% and yet even more desirably no more than about 35% when subjected to the Z-Direction Lotion Migration Test set forth below. In articles which have a greater z-direction migration loss, the hydrophilic lotion formulation undesirably migrates into the interior and along the surface of the bodyside liner and at times through the bodyside liner into the absorbent body of the article which results in a lower reduction in abrasion and less transfer to the skin of the wearer.

Another important measure of the hydrophilic lotion formulations of the different aspects of the present invention is their ability to resist migration laterally along the surface of the bodyside liner. In this regard, the articles having the hydrophilic lotion formulations of the present invention applied to there bodyside liner define a cd-direction migration loss of no more than about 40%, desirably no more than about 35%, more desirably no more than about 30%, even more desirably no more than about 25% and yet even more desirably no more than about 20% when subjected to the CD-Direction Lotion Migration Test set forth below. In articles which have a greater cd-direction migration loss, the lotion formulation undesirably migrates along the surface of the bodyside liner and at times through the bodyside liner into the absorbent body of the article which results in a lower reduction in abrasion and less transfer to the skin of the wearer.

Moreover, to provide the improved stability and transfer to the skin of the wearer, the hydrophilic lotion formulation of the present invention may define a melting point of from about 30° C. to about 100° C. , desirably from about 40° C. to about 80° C., and more desirably from about 50° C. to about 60° C. Hydrophilic lotion formulations which have lower melting points exhibit migration of the hydrophilic lotion during use and at elevated temperatures in storage which can undesirably result in reduced transfer to the skin. Whereas, hydrophilic lotion formulations which have higher melting points may require that the hydrophilic lotion be at a temperature above the flash point of the bodyside liner material which can undesirably lead to fires.

The hydrophilic lotion formulation of the present invention may further define a melt point viscosity of from about 20 to about 1000000 centipoise, desirably from about 50 to about 10000 centipoise, and more desirably from about 100 to about 500 centipoise for reduced migration and improved transfer to the skin of the wearer. Hydrophilic lotion formulations which have lower melt point viscosities exhibit migration of the hydrophilic lotion through the bodyside liner into the absorbent body of the article which can undesirably result in reduced transfer to the skin. Whereas, hydrophilic lotion formulations which have higher melt point viscosities may be so solid as to also exhibit a reduced transfer to the skin.

Further, to provide the improved stability and transfer to the skin of the wearer, the hydrophilic lotion formulation of the present invention may also define a viscosity of from about 10 to about 10,000 centipoise, desirably from about 50 to about 500 centipoise, and more desirably from about 75 to about 250 centipoise at a temperature of 60° C. Hydrophilic lotion formulations which have lower viscosities at 60° C. exhibit migration of the hydrophilic lotion through the bodyside liner into the absorbent body of the article which can undesirably result in reduced transfer to the skin. Whereas, hydrophilic lotion formulations which have higher viscosities at 60° C. may be so solid as to also exhibit a reduced transfer to the skin.

The penetration hardness of the hydrophilic lotion formulations of this invention can be from about 5 to about 360 millimeters, more desirably from about 5 to about 200 millimeters, more desirably from about 5 to about 150 millimeters, and still more desirably from about 5 to about 100 millimeters. (Hydrophilic lotion formulations having a needle penetration hardness greater than 360 millimeters cannot be measured using ASTM method D 1321). The hardness of the hydrophilic lotion formulations of this invention is important for two reasons. First, the softer the formulation the more mobile the formulation will be, making the formulation more likely to migrate to the inner plies of the tissue, which is not desirable. Secondly, softer formulations tend to be more greasy/oily to the touch, which is also less desirable. In general, formulations having a needle penetration hardness of from about 200 to about 360 millimeters feel creamy to slightly greasy with less smoothness (depending on additives). Formulations that have needle penetration hardness values of from about 5 to about 200 millimeters feel silky to creamy and very smooth (depending on additives).

Figure 3:
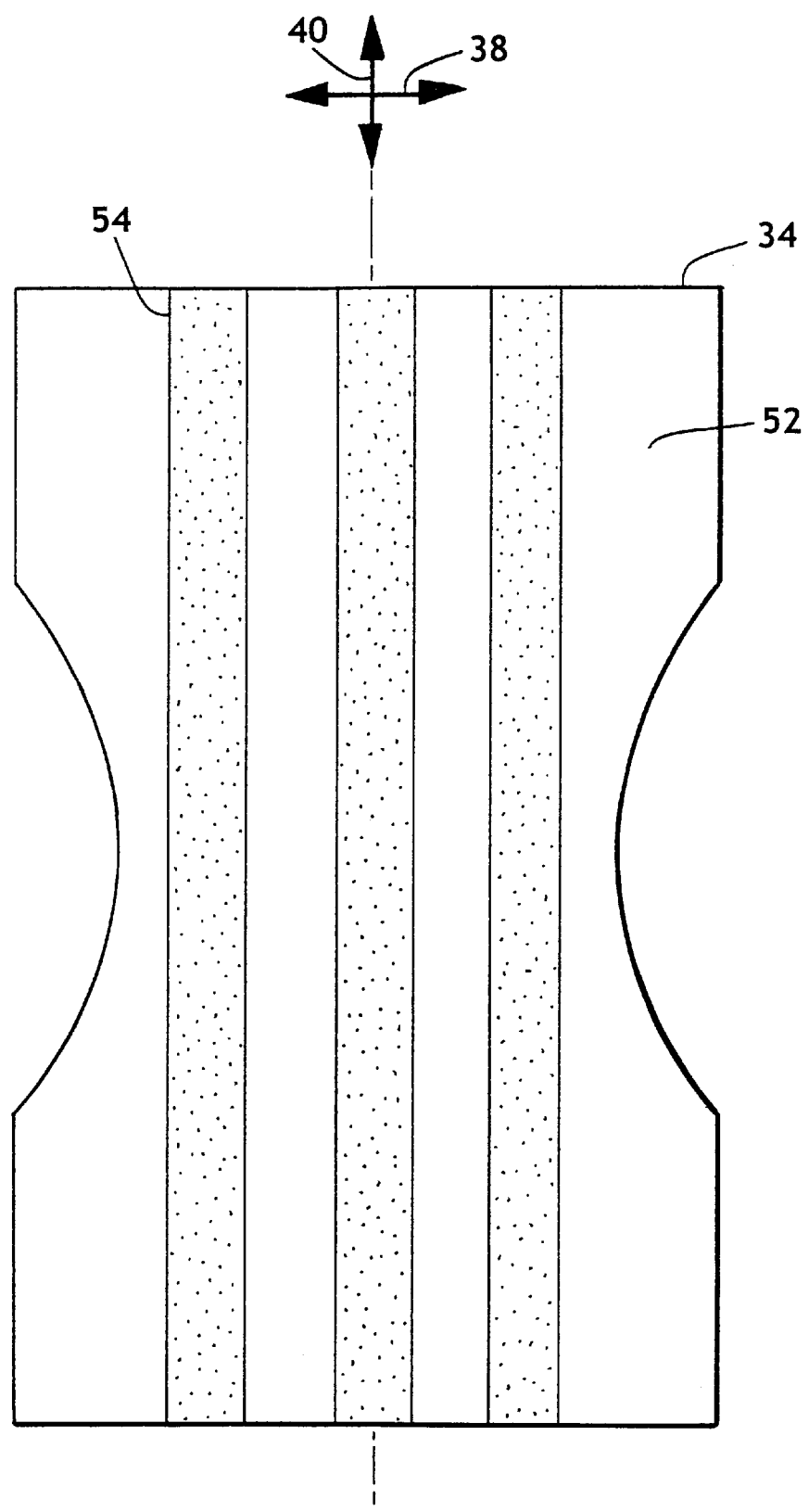
FIG. 3 representatively shows a top plan view of the bodyside liner of the absorbent article of FIG. 1 with the surface which contacts the wearer facing the viewer.

The hydrophilic lotion formulation may be applied to the entire bodyfacing surface 52 of the bodyside liner 34 or may be selectively applied to particular sections of the bodyfacing surface 52, such as the medial section along the longitudinal centerline of the diaper, to provide greater lubricity of such sections and to transfer such hydrophilic lotion to the wearer's skin. Alternatively, as representatively illustrated in FIG. 3, the bodyfacing surface 52 of the bodyside liner 34 may include multiple stripes 54 of the hydrophilic lotion formulation applied thereto. For example, the bodyfacing surface 52 of the bodyside liner 34 may include from 1 to 10 stripes 54 of hydrophilic lotion formulation extending along the longitudinal direction 40 of the diaper 20. The stripes 54 may extend the full length of the bodyside liner 34 or only a portion thereof. The stripes 54 may also define a width of from about 0.20 to about 1 centimeters.

The hydrophilic lotion formulation should cover a sufficient amount of the surface area of the bodyside liner 34 to ensure adequate transfer to the skin and reduced abrasion between the liner 34 and the wearer's skin. Desirably, the hydrophilic lotion formulation is applied to at least about 5 percent and more desirably at least about 25 percent of the bodyside liner 34 for improved transfer.

The hydrophilic lotion formulation can be applied to the bodyside liner at any add-on level which provides the desired transfer benefit. For example, the total add-on level of the lotion formulation can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the hydrophilic lotion on the product attributes and the specific hydrophilic lotion formulation. As discussed above, the improved stability and reduced tendency to migrate of the hydrophilic lotion formulations of the present invention allows a lesser amount of hydrophilic lotion to be applied to the liner 34 to achieve the same benefit when compared with conventional hydrophilic lotion formulations. Moreover, the hydrophilic nature of the lotion formulation can allow a higher add-on level over a greater surface area since it has a reduced adverse impact on the absorbency and liquid uptake properties of the bodyside liner 34 and absorbent body 36. The higher add-on and greater surface area can result in more transfer to the skin for improved skin health.

The hydrophilic lotion formulation may be applied to the bodyside liner 34 in any of many well known manners. A preferred method to uniformly apply the hydrophilic lotion formulation to the surface of the bodyside liner 34 is spraying or slot coating which offers maximum control of the formulation distribution and transfer rate. However, other methods, such as flexographic printing, rotogravure printing or extrusion, can be used.

For example, the hydrophilic lotion formulation may be applied to the bodyside liner 34 by (a) heating the hydrophilic lotion formulation to a temperature above the melting point of the formulation, causing the formulation to melt, (b) uniformly applying the melted formulation to the bodyfacing surface of the bodyside liner; and (c) resolidifying the deposits of the melted formulation. Desirably, resolidification of the deposits occurs almost instantaneously, without the need for external cooling means such as chill rolls. This can occur if the formulation is heated to a temperature only slightly above or at the melting point of the formulation. However, external means such as chill rolls, either before or after the application of melt, can be used if desired to accelerate resolidification.

The increased viscosity of the lotion at the process temperature and the instantaneous resolidification tends to impede penetration of the formulation into the bodyside liner and absorbent body of the article and retain it on the bodyfacing surface 52 of the bodyside liner 34, which is advantageous. For example, the temperature of the melted formulation can advantageously be less than about 10° C., more desirably less than about 5° C., and still more desirably less than about 2° C. above the melting point of the formulation prior to applying it to the bodyside liner for reduced migration. As the temperature of the melted formulation approaches the melting point of the formulation, the viscosity of the melted formulation increases, which further enhances the tendency of the melted formulation to be retained on the surface.

Accordingly, the present invention provides absorbent articles having bodyside liners which incorporate a hydrophilic lotion formulation on the bodyfacing surface thereof. Since the hydrophilic lotion formulations applied to the liner of the absorbent articles of the present invention are hydrophilic, the absorbent articles have maintained high levels of absorbency and rapid liquid intake. As such, the hydrophilic lotions can be applied in greater amounts and over greater percentages of the overall surface area on the bodyside liner for improved transfer to the skin and resulting skin health. As a result, the skin of the wearers of such absorbent articles should remain less susceptible to rashes, abrasion and irritation.

Moreover, because the hydrophilic lotion formulation is a solid at room temperature, has increased viscosity at process temperature and rapidly solidifies after deposition, it has less tendency to penetrate and migrate into the liner and absorbent body of the article during processing and at elevated storage temperatures. Compared to liners treated with liquid or semi-solid formulations, the hydrophilic lotion formulations of the present invention leave a greater percentage of the added formulation on the bodyfacing surface of the liner where it can contact and transfer to the wearer's skin to provide a benefit. The high melt point viscosity of the hydrophilic lotion formulations of the present invention also assists in reducing the migration of the hydrophilic lotion into the article. Accordingly, absorbent articles having the hydrophilic lotionized bodyside liners of the present invention are able to provide an improved skin health benefit to the wearer on a cost effective basis.

Test Methods
Z-Direction Lotion Migration Test

This test determines the quantity of lotion which remains on the target area of the bodyfacing surface of an absorbent article after a given period of time at a given temperature. Specifically, the purpose of the test is to compare the amount of lotion present in the target zone on articles stored at a lower temperature with that present on articles stored at a higher temperature. The test simulates storage at elevated temperature conditions which may occur to such articles. For example, such articles may be stored in the trunk of a vehicle or in a warehouse in a warm climate such as in a warehouse in Arizona in July or August. The z-direction migration loss is a measure of the lotion migration after storage at 130° F. when compared to the lotion migration at 73° F. after a fixed period of time. Thus, this test predicts the amount of lotion which will be available on the bodyfacing surface of the article for transfer to the skin when the article is used as well as how quickly it will undesirably migrate away from or along the bodyfacing surface of the article in use.

Specifically, the test is conducted as follows:

1. Ten (10) products having a lotion formulation applied to the bodyside liner are obtained.

2. Five (5) products are placed in a controlled environment at a temperature of 73° F. and a relative humidity of 50% for a fixed period of time such as, for example, 28 days. The other five (5) products are placed in a controlled environment at a temperature of 130° F. and ambient humidity for the same period of time.

3. The products are removed from the controlled environment and a sample of the bodyside liner having a width of 3.75 inches and a length of 13 inches is removed from the center of each product.

Figure 4:
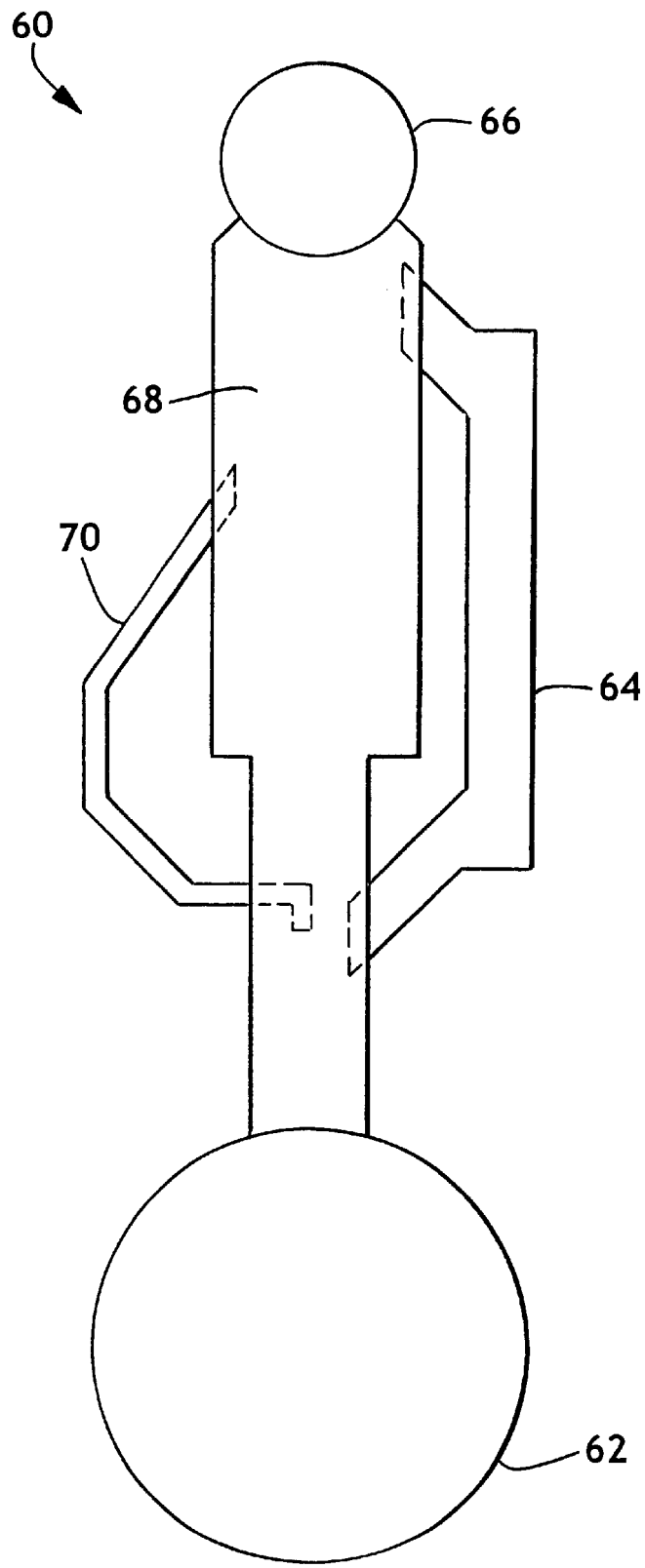
FIG. 4 representatively shows the test apparatus for the Lotion Migration Test set forth herein.

4. The samples are then subjected to Soxhlet Extraction with Gravimetric Analysis (SEGA) as follows. A SEGA test apparatus such as that representatively illustrated in FIG. 4 is used. The test apparatus 60 includes a reboiler 62, chloroform vapor duct 64, cold water condenser 66, holding tank 68 where the samples are placed and a chloroform recycle duct 70. The components of the test apparatus are conventional glassware well known to those skilled in the art. For example, the reboiler may include a 250 ml round-bottom flask and the vapor duct can include an 85 ml soxlet. A sample is placed in the holding tank 68 and subjected to chloroform washing cycles for 2.5 hours. 125 milliliters of liquid chloroform is placed in the reboiler. The chloroform vaporizes and rises up through the vapor duct 64 into the condenser 66 having tap water therein which, in turn, causes the chloroform to liquefy and fall into the holding tank 68 with the sample. The chloroform dissolves the lotion from the liner sample. When the liquid chloroform reaches a high enough level, the recycle duct returns the chloroform/lotion mixture to the reboiler. The temperature in the reboiler is controlled such that it is above the boiling point of the chloroform but below that of the lotion such that only the chloroform vaporizes to start the process over again. One complete wash cycle takes approximately 15 minutes with about 75 milliliters of chloroform circulating through the liner sample in each cycle. Upon completion, the chloroform in the evaporator is evaporated utilizing a conventional vacuum evaporator such as a rotovap commercially available under the model number Buchi 011 RE 121 for a period of 4 minutes followed by placing the lotion in an aluminum pan and heating on a hot plate with forced air circulation for an additional 30 minutes.

5. The residue (lotion) remaining for each sample is then weighed. The amount of lotion recovered from the products stored at 73° F. is then compared to the amount of lotion recovered from the products stored at 130° F. to determine the stability of the lotion formulation at high temperature.

The z-direction migration loss of the absorbent article is then determined as follows:

$$\text{Z-direction migration loss } (\%) = [(L_{73} - L_{130})/L_{73}] \times 100$$

wherein, $L_{73}$=average weight (g) of lotion recovered per sample stored at 73° F.

$L_{130}$=average weight (g) of lotion recovered per sample stored at 130° F.

CD-Direction Lotion Migration Test

This test determines the quantity of lotion which remains on the specific location where it is applied on the bodyfacing surface of an absorbent article after a given period of time at a given temperature. Specifically, the purpose of the test is to compare the amount of lotion present in the applied location on the bodyside liner with that present on the remaining portions of the bodyside liner of the articles after being stored at an elevated temperature. The test simulates storage at elevated temperature conditions which may occur to such articles. For example, such articles may be stored in the trunk of a vehicle or in a warehouse in a warm climate such as in a warehouse in Arizona in July or August. The cd-direction migration loss is a measure of the lateral lotion migration along the bodyfacing surface of the article after storage at 130° F. after a fixed period of time. Thus, this test predicts the amount of lotion which will be available in the desired location on the bodyfacing surface of the article for transfer to the skin when the article is used as well as how quickly it will undesirably migrate away from or along the bodyfacing surface of the article in use.

Specifically, the test is conducted as follows:

1. Five (5) products having a lotion formulation applied to the bodyside liner in a specific pattern are obtained.

2. The products are placed in a controlled environment at a temperature of 130° F. and ambient humidity for a fixed period of time such as, for example, 28 days.

3. The products are removed from the controlled environment and the bodyside liner on each product is removed and dissected to remove the portion of the liner to which the lotion was actually applied. For example, if the lotion was applied as 4 continuous lines having a width of 0.25 inches with spaces of 0.75 inches in between, the 4 strips of liner would be removed.

4. The samples which include the portions of the liner to which the lotion was applied are then grouped together and subjected to Soxhlet Extraction with Gravimetric Analysis (SEGA) as described above. The remaining portions of the bodyside liner are also grouped together and subjected to a separate SEGA extraction.

5. The residue (lotion) remaining for each group is then weighed. The amount of lotion recovered from the portions of the bodyside liner to which the lotion was applied is then compared to the amount of lotion recovered from the remaining portions of the bodyside liner to determine the stability of the lotion formulation at high temperature.

The cd-direction migration loss of the absorbent article is then determined as follows:

$$\text{CD-direction migration loss } (\%) = [L_{sp}/(L_a + L_{sp})] \times 100$$

wherein, $L_{sp}$ average weight (g) of lotion recovered from the portions of the bodyside liner to which the lotion was not applied per diaper $L_a$=average weight (g) of lotion recovered from the portions of the bodyside liner to which the lotion was applied per diaper Water Vapor Transmission Test A suitable technique for determining the WVTR (water vapor transmission rate) value of a material is as follows. For the purposes of the present invention, 3-inch diameter (76 millimeter) circular samples are cut from the test material and from a control material, Celguard® 500 (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test } WVTR = [(\text{grams weight loss over 24 hours}) \times 7571](g/m^2/24 \text{ hours})$$

The relative humidity within the oven is not specifically controlled. Under predetermined set conditions of 100° F. and ambient relative humidity, the WVTR for Celguard 2500 has been determined to be 5000 g/m$^2$/24 hours. Accordingly, Celguard 2500 is run as a control sample with each test. Celguard 2500 is a 0.0025 cm thick film composed of a microporous polypropylene.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

What is claimed is:

1. An absorbent article comprising:

a) an outer cover;

b) a liquid permeable bodyside liner which defines a bodyfacing surface and which is connected in superposed relation to said outer cover;

c) an absorbent body which is located between said bodyside liner and said outer cover; and d) a hydrophilic lotion formulation on at least a portion of said bodyfacing surface of said bodyside liner which includes from about 10 to about 90 weight percent of a hydrophilic solvent, from about 5 to about 90 weight percent of a high molecular weight polyethylene glycol, and from about 0 to about 60 weight percent of a fatty alcohol based on a total weight of said hydrophilic lotion formulation, wherein said absorbent article defines a z-direction migration loss of said hydrophilic lotion formulation of no more than about 55%.

2. The absorbent article according to claim 1 wherein said hydrophilic solvent is selected from the group consisting of water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol, hydrogenated starch hydrolysate, silicone glycols, and mixtures thereof.

3. The absorbent article according to claim 1 wherein said hydrophilic solvent is selected from the group consisting of propylene glycol, low molecular weight polyethylene glycol and mixtures thereof.

4. The absorbent article according to claim 1 wherein said high molecular weight polyethylene glycol is selected from the group consisting of PEG 6000 polyethylene glycol, PEG 8000 polyethylene glycol, PEG 10000 polyethylene glycol and mixtures thereof.

5. The absorbent article according to claim 1 wherein said fatty alcohol is selected from the group consisting of alcohols having a carbon chain length of $C_{14}$–$C_{30}$ and mixtures thereof.

6. The absorbent article according to claim 1 wherein said fatty alcohol is selected from the group consisting of stearyl alcohol, behenyl alcohol and mixtures thereof.

7. The absorbent article according to claim 1 wherein said hydrophilic lotion formulation further comprises from about 0 to about 25 weight percent of a viscosity enhancer.

8. The absorbent article according to claim 7 wherein said viscosity enhancer increases a viscosity of said lotion formulation by at least about 50 percent at a temperature of 60° C.

9. The absorbent article according to claim 1 wherein said hydrophilic lotion formulation defines a viscosity of from about 10 to about 10.000 centipoise at a temperature of 60° C.

10. The absorbent article according to claim 1 wherein said hydrophilic lotion formulation defines a melt point viscosity of from about 20 to about 1,000,000 centipoise.

11. The absorbent article according to claim 1 wherein said hydrophilic lotion formulation defines a melting point of from about 30 to about 100° C.

12. The absorbent article according to claim 1 wherein said hydrophilic lotion formulation is applied to said bodyside liner at a temperature no more than about 10° C. above a melting point of said hydrophilic lotion formulation to reduce migration of said hydrophilic lotion formulation.

13. The absorbent article according to claim 1 wherein said hydrophilic lotion formulation is applied t o said bodyside liner at a temperature no more than about 5° C. above a melting point of said hydrophilic lotion formulation to reduce migration of said hydrophilic lotion formulation.

14. An absorbent article comprising:
a) an outer cover;
b) a liquid permeable bodyside liner which defines a bodyfacing surface and which is connected in superposed relation to said outer cover;
c) an absorbent body which is located between said bodyside liner and said outer cover; and
d) a hydrophilic lotion formulation on at least a portion of said bodyfacing surface of said bodyside liner which includes from about 10 to about 90 weight percent of a hydrophilic solvent and from about 5 to about 90 weight percent of a high molecular weight polyethylene glycol, wherein said absorbent article defines a z-direction migration loss of said hydrophilic lotion formulation of no more than about 55%.

15. The absorbent article according to claim 14 wherein said hydrophilic solvent is selected from the group consisting of water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol, hydrogenated starch hydrolysate, silicone glycols, and mixtures thereof.

16. The absorbent article according to claim 14 wherein said hydrophilic solvent is selected from the group consisting of propylene glycol or low molecular weight polyethylene glycol and mixtures thereof.

17. The absorbent article according to claim 14 wherein said high molecular weight polyethylene glycol is selected from the group consisting of PEG 6000 polyethylene glycol, PEG 8000 polyethylene glycol, PEG 10000 polyethylene glycol and mixtures thereof.

18. The absorbent article according to claim 14 wherein said lotion further includes a fatty alcohol selected from the group consisting of alcohols having a carbon chain length of $C_{14}$–$C_{30}$ and mixtures thereof.

19. The absorbent article according to claim 18 wherein said fatty alcohol is selected from the group consisting of stearyl alcohol, behenyl alcohol and mixtures thereof.

20. The absorbent article according to claim 14 wherein said hydrophilic lotion formulation defines a viscosity of from about 10 to about 10,000 centipoise at a temperature of 60° C.

21. The absorbent article according to claim 14 wherein said hydrophilic lotion formulation defines a melt point viscosity of from about 20 to about 1,000,000 centipoise.

22. The absorbent article according to claim 14 wherein said hydrophilic lotion formulation defines a melting point of from about 30 to about 100° C.

23. The absorbent article according to claim 14 wherein said z-direction migration loss of said absorbent article is no more than about 50%.

24. The absorbent article according to claim 14 wherein said absorbent article defines a cd-direction migration loss of no more than about 40%.

25. The absorbent article according to claim 14 wherein said hydrophilic lotion formulation is applied to said bodyside liner at a temperature no more than about 10° C. above a melting point of said hydrophilic lotion formulation to reduce migration of said hydrophilic lotion formulation.

26. The absorbent article according to claim 14 wherein said hydrophilic lotion formulation further comprises a viscosity enhancer.

27. The absorbent article according to claim 26 wherein said viscosity enhancer increases a viscosity of said lotion formulation by at least about 50 percent at a temperature of 60° C.

28. An absorbent article comprising:
a) an outer cover;
b) a liquid permeable bodyside liner which defines a bodyfacing surface and which is connected in superposed relation to said outer cover;
c) an absorbent body which is located between said bodyside liner and said outer cover; and
d) a hydrophilic lotion formulation on at least a portion of said bodyfacing surface of said bodyside liner which includes i) from about 30 to about 70 weight percent of a solvent, selected from the group consisting of propylene glycol, low molecular weight polyethylene glycol and mixtures thereof based on a total weight of said hydrophilic lotion formulation;

ii) from about 15 to about 25 weight percent of a polyethylene glycol selected from the group consisting of PEG 6000 polyethylene glycol, PEG 8000 polyethylene glycol, PEG 10000 polyethylene glycol and mixtures thereof based on a total weight of said hydrophilic lotion formulation; and iii) from about 15 to about 25 weight percent of a fatty alcohol selected from the group consisting of stearyl alcohol, behenyl alcohol and mixtures thereof based on said total weight of said hydrophilic lotion formulation, wherein the absorbent article defines a z-direction migration loss of said hydrophilic lotion formulation of no more than about 55%.

29. The absorbent article according to claim 28 wherein said hydrophilic lotion formulation defines a viscosity of from about 10 to about 10,000 centipoise at a temperature of 60° C.

30. The absorbent article according to claim 28 wherein said hydrophilic lotion formulation defines a melt point viscosity of from about 20 to about 1,000,000 centipoise.

31. The absorbent article according to claim 28 wherein said hydrophilic lotion formulation defines a melting point of from about 30 to about 100° C.

32. The absorbent article according to claim 28 wherein said hydrophilic lotion formulation is applied to said bodyside liner at a temperature no more than about 10° C. above a melting point of said hydrophilic lotion formulation to reduce migration of said hydrophilic lotion formulation.

33. The absorbent article according to claim 28 wherein said hydrophilic lotion formulation is applied to said bodyside liner at a temperature no more than about 5° C. above a melting point of said hydrophilic lotion formulation to reduce migration of said hydrophilic lotion formulation.

* * * * *